US00PP20063P2

(12) United States Plant Patent
Jandrew

(10) Patent No.: US PP20,063 P2
(45) Date of Patent: Jun. 9, 2009

(54) ***GOODENIA* PLANT NAMED 'FRES YEL'**

(50) Latin Name: *Goodenia ovata*
Varietal Denomination: Fres Yel

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/150,465

(22) Filed: Apr. 28, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
(74) *Attorney, Agent, or Firm*—C. A. Whealy

(57) ABSTRACT

A new and distinct cultivar of *Goodenia* plant named 'Fres Yel', characterized by its dense and bushy, mounded, outwardly spreading to prostrate plant habit; freely branching habit; freely flowering habit; bright yellow-colored flowers; and good garden performance.

2 Drawing Sheets

Botanical designation: *Goodenia ovata.*
Cultivar denomination: 'FRES YEL'.

BACKGROUND OF THE INVENTION

The present invention relates to a new and distinct cultivar of *Goodenia,* botanically known as *Goodenia ovata,* and hereinafter referred to by the name 'Fres Yel'.

The new *Goodenia* is a product of a planned breeding program conducted by the Inventor in Gilroy, Calif. The objective of the breeding program is to create new freely-flowering *Goodenia* cultivars with uniform plant habit and attractive flower coloration.

The new *Goodenia* originated from a cross-pollination made by the Inventor in Gilroy, Calif. in August, 2004 of a proprietary selection of *Goodenia ovata* identified as code number 105, not patented, as the female, or seed, parent with a proprietary selection of *Goodenia ovata* identified as code number 101-3, not patented, as the male, or pollen, parent. Seeds resulting from the crossing were sown in May, 2005. The new cultivar *Goodenia* was discovered and selected by the Inventor as a single flowering plant within the progeny of the stated cross-pollination in a controlled greenhouse environment in Gilroy, Calif. in September, 2005.

Asexual reproduction of the new *Goodenia* by terminal cuttings in a controlled greenhouse environment in Gilroy, Calif. since September, 2005, has shown that the unique features of this new *Goodenia* are stable and reproduced true to type in successive generations.

SUMMARY OF THE INVENTION

Plants of the new *Goodenia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fres Yel'. These characteristics in combination distinguish 'Fres Yel' as a new and distinct cultivar of *Goodenia:*

1. Dense and bushy, mounded, outwardly spreading to prostrate plant habit.
2. Freely branching habit.
3. Freely flowering habit.
4. Bright yellow-colored flowers.
5. Good garden performance.

Plants of the new *Goodenia* can be compared to plants of the female parent selection. Plants of the new *Goodenia* differ from plants of the female parent selection in the following characteristics:

1. Plants of the new *Goodenia* have shorter internodes than plants of the female parent selection.
2. Plants of the new *Goodenia* have smaller leaves than plants of the female parent selection.
3. Plants of the new *Goodenia* are more freely flowering than plants of the female parent selection.

Plants of the new *Goodenia* can be compared to plants of the male parent selection. Plants of the new *Goodenia* differ from plants of the male parent selection in the following characteristics:

1. Plants of the new *Goodenia* have shorter internodes than plants of the male parent selection.
2. Plants of the new *Goodenia* have larger leaves than plants of the male parent selection.
3. Plants of the new *Goodenia* are more freely flowering than plants of the male parent selection.

Plants of the new *Goodenia* can be compared to plants of the *Goodenia ovata* 'Lime Twist', not patented. In side-by-side comparisons conducted in Gilroy, Calif., plants of the new *Goodenia* differed from plants of 'Lime Twist' in the following characteristics:

1. Plants of the new *Goodenia* had shorter internodes than plants of 'Lime Twist'.
2. Plants of the new *Goodenia* were more freely flowering than plants of 'Lime Twist'.
3. Plants of the new *Goodenia* had larger flowers than plants of 'Lime Twist'.

BRIEF DESCRIPTION OF THE PHOTOGRAPHS

The accompanying colored photographs illustrate the overall appearance of the new *Goodenia,* showing the colors as true as it is reasonably possible to obtain in colored reproductions of this type. Colors in the photographs may differ slightly from the color values cited in the detailed botanical description which accurately describe the colors of the new *Goodenia.*

The photograph on the first sheet is a side perspective view of a typical flowering plant of 'Fres Yel' grown in a container.

The photograph on the second sheet comprises a close-up view of typical flowers and leaves of 'Fres Yel'. Plants used for the photographs were grown in Gilroy, Calif. during the spring in 20-cm containers in a greenhouse and under cultural conditions typical of *Goodenia* production. Plants were pinched one time and were seven months old when the photographs were taken.

DETAILED BOTANICAL DESCRIPTION

The following observations, measurements and values describe plants grown in Gilroy, Calif. in 30-cm containers in a greenhouse during the summer and under conditions which closely approximate commercial production. Plants were pinched one time and were seven months old when the description was taken. In the description, color references are made to The Royal Horticultural Society Colour Chart, 2001 Edition, except where general terms of ordinary dictionary significance are used.

Botanical classification: *Goodenia ovata* 'Fres Yel'.

Parentage:

*Female, or seed, parent.*—Proprietary selection of *Goodenia ovata* identified as code number 105, not patented.

*Male or pollen parent.*—Proprietary selection of *Goodenia ovata* identified as code number 101-3, not patented.

Propagation:

*Type.*—By vegetative cuttings.

*Time to initiate and develop roots.*—About three weeks.

*Root description.*—Fibrous.

*Rotting habit.*—Freely branching.

Plant description:

*Plant form and growth habit.*—Dense and bushy, mounded, outwardly spreading to prostrate plant habit. Vigorous growth habit.

*Branching habit.*—Freely branching habit; when pinched, lateral branches potentially develop at every node.

*Plant height.*—About 10 cm to 13 cm.

*Plant diameter* (*area of spread*).—About 50 cm to 55 cm.

Lateral branch description:

*Length.*—About 40 cm to 55 cm.

*Diameter.*—About 2 mm.

*Internode length.*—About 1.5 cm to 1.8 cm.

*Texture.*—Slightly hirsute with glandular hairs.

*Color.*—Slightly more green than 148A.

Foliage description:

*Arrangement.*—Alternate, simple.

*Length.*—About 4.2 cm to 4.5 cm.

*Width.*—About 2.4 cm to 2.7 cm.

*Shape.*—Ovate.

*Apex.*—Acute.

*Base.*—Attenuate.

*Margin.*—Serrulate.

*Texture upper and lower surfaces.*—Slightly hirsute with glandular hairs.

*Venation pattern.*—Pinnate.

*Color.*—Developing foliage, upper and lower surfaces: Close to 146A. Fully expanded foliage, upper surface: Close to 137B; venation, close to 144A. Fully expanded foliage, lower surface: Close to 137C; venation, close to 144A.

*Petiole.*—Length: About 7 mm to 9 mm. Diameter: About 1 mm. Texture, upper and lower surfaces: Slightly hirsute with glandular hairs. Color, upper and lower surfaces: Close to 144A.

Flower description:

*Flower arrangement.*—Single flowers arranged on terminal clusters with two to three flowers per cluster; flowers bilabiate with two banner petals and three lower petals. Freely flowering habit with usually about 200 flower clusters per plant. Flowers face upright and outwardly. Flowers not fragrant.

*Natural flowering season.*—Plants flower freely and continuously from the spring into the fall in California. Flowers last about one week on the plant. Flowers not persistent.

*Flower diameter.*—About 2.2 cm to 2.3 cm.

*Flower height.*—About 2.5 cm to 2.7 cm.

*Flower bud.*—Length: About 1 cm to 1.3 cm. Diameter: About 2 mm to 3 mm. Shape: Oblong. Color: Towards the apex, close to N144A; towards the base, close to N144B.

*Corolla.*—

*Arrangement.*—Flowers bilabiate with corolla consists of five petals modified into two banner petals and three lower petals. Banner petal length: About 1.7 cm. Banner petal width: About 8 mm to 9 mm. Lower petal length: About 2.3 cm. Lower petal width: About 6 mm to 8 mm. Banner and lower petal shape: Spatulate. Banner and lower petal apex: Emarginate. Banner and lower petal base: Cuneate. Banner and lower petal margin: Entire; slightly undulate. Banner and lower petal texture, upper and lower surfaces: Papillose. Banner and lower petal color: When opening, upper and lower surfaces: Between 6A and 7A. Fully developed, upper surface: Close to 6A. Fully developed, lower surface: Close to 5A; basal vertical lines, close to 22C.

*Sepals.*—Appearance: Five sepals fused into a star-shaped calyx. Length: About 5 mm. Width: About 1 mm. Shape: Lanceolate. Apex: Acute. Base: Attenuate. Margin: Entire. Texture, upper and lower surfaces: Slightly hirsute. Color, upper and lower surfaces: Close to 146A.

*Peduncles.*—Length: About 1.5 cm to 1.7 cm. Diameter: Less than 1 mm. Texture: Smooth, glabrous. Color: Close to 146A.

*Pedicels.*—Length: About 7 mm to 10 mm. Diameter: Less than 1 mm. Texture: Smooth, glabrous. Color: Close to 146A.

*Reproductive organs.*—Androecium: Stamen number per flower: About five. Filament length: About 6 mm to 7 mm. Filament color: Close to 2D. Anther color: Close to 165A. Amount of pollen: Moderate. Pollen color: Close to 8D. Gynoecium: Pistil number per flower: One. Pistil length: About 8 mm to 10 mm.

Style length: About 8 mm. Style color: Close to 2D. Stigma color: Close to 144A; towards the apex, close to 2D.

*Seed/fruit.*—Seed and fruit production have not been observed.

Garden performance: Plants of the new *Goodenia* have been observed to have good garden performance and tolerate rain, wind and a wide range of temperatures.

Pathogen/pest resistance: Plants of the new *Goodenia* have not been shown to be resistant to pathogens and pests common to *Goodenia*.

It is claimed:

1. A new and distinct *Goodenia* plant named 'Fres Yel' as illustrated and described.

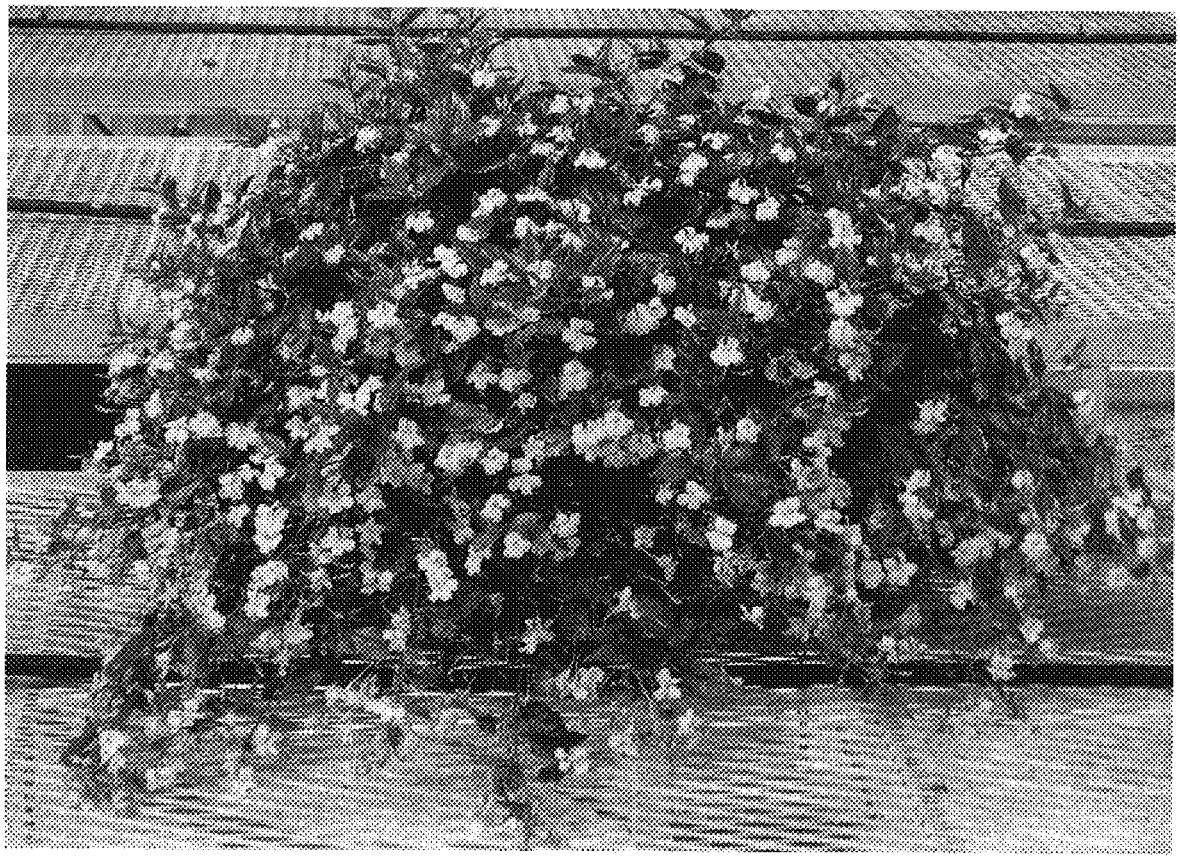

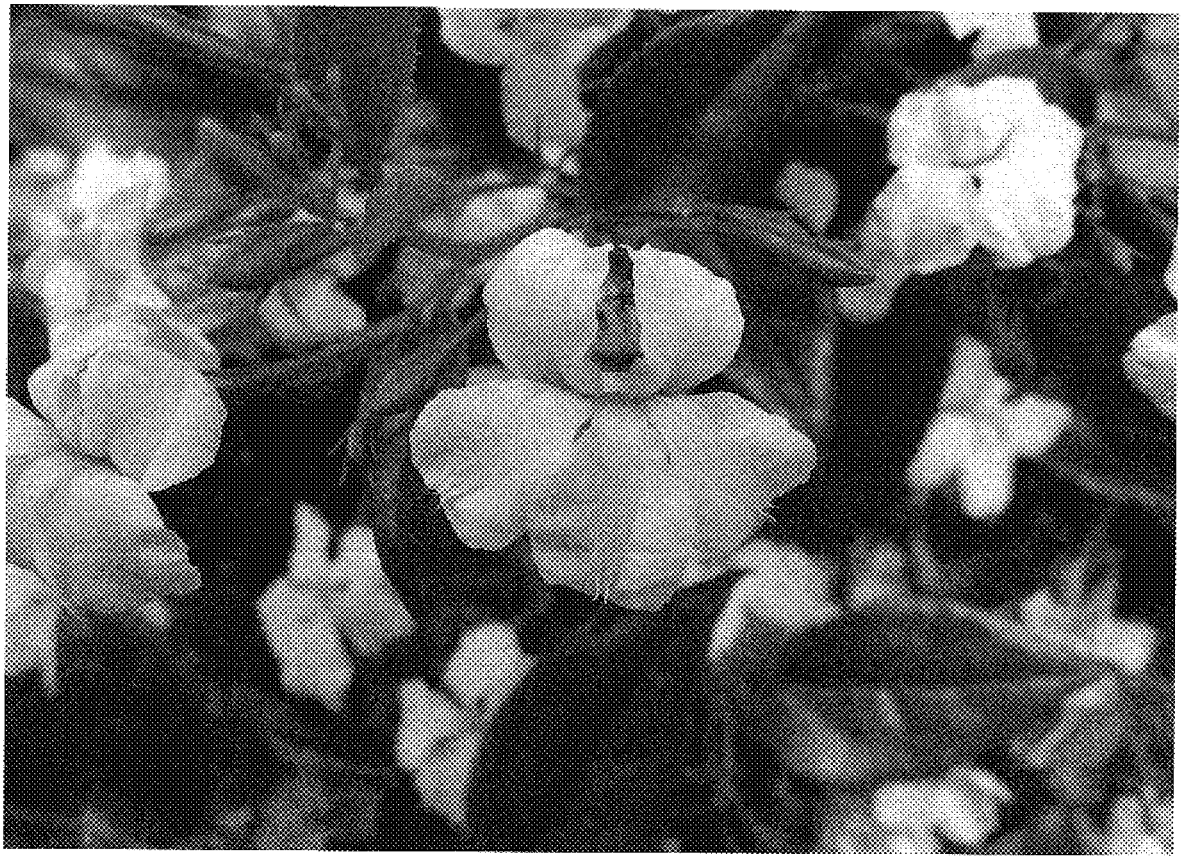

* * * * *